(12) United States Patent
Urich et al.

(10) Patent No.: US 11,000,411 B2
(45) Date of Patent: May 11, 2021

(54) OCCLUSION-ACTIVATED HEAT SUPPRESSION INFUSION SLEEVE

(71) Applicants: Alex Urich, Coto de Caza, CA (US); Armand Maaskamp, Scottsdale, AZ (US); Ryan Maaskamp, Scottsdale, AZ (US)

(72) Inventors: Alex Urich, Coto de Caza, CA (US); Armand Maaskamp, Scottsdale, AZ (US); Ryan Maaskamp, Scottsdale, AZ (US)

( * ) Notice: Subject to any disclaimer, the term of this patent is extended or adjusted under 35 U.S.C. 154(b) by 0 days.

(21) Appl. No.: 16/829,102

(22) Filed: Mar. 25, 2020

(65) Prior Publication Data

US 2020/0222237 A1 Jul. 16, 2020

Related U.S. Application Data

(62) Division of application No. 14/450,107, filed on Aug. 1, 2014, now abandoned.

(60) Provisional application No. 61/861,879, filed on Aug. 2, 2013.

(51) Int. Cl.
*A61F 9/00* (2006.01)
*A61F 9/007* (2006.01)
*A61M 3/02* (2006.01)
*A61B 17/32* (2006.01)
*A61M 1/00* (2006.01)
*A61B 18/00* (2006.01)

(52) U.S. Cl.
CPC .. *A61F 9/00745* (2013.01); *A61B 17/320068* (2013.01); *A61M 1/008* (2013.01); *A61M 3/0216* (2014.02); *A61M 3/0241* (2013.01); *A61M 3/0283* (2013.01); *A61B 2017/32007* (2017.08); *A61B 2017/320084* (2013.01); *A61B 2018/00035* (2013.01); *A61M 2205/3606* (2013.01); *A61M 2210/0612* (2013.01)

(58) Field of Classification Search
CPC ......... A61B 2017/320084; A61B 2018/00035; A61B 17/320068; A61B 2017/32007; A61M 5/31515; A61M 1/008; A61M 2210/0612; A61M 3/0283; A61F 9/00745
See application file for complete search history.

(56) References Cited

U.S. PATENT DOCUMENTS

| 5,171,307 | A | * | 12/1992 | Sanning | A61M 3/0287 604/327 |
| 5,387,201 | A | * | 2/1995 | Fowler | A61M 3/0279 604/290 |
| 5,505,693 | A | * | 4/1996 | Mackool | A61F 9/00745 604/22 |

(Continued)

*Primary Examiner* — William R Carpenter
(74) *Attorney, Agent, or Firm* — Kenneth Altshuler (57) ABSTRACT

Described is a phacoemulsification device for eye surgery that generally comprises an ultrasonically vibrating aspiration needle that withdraws ocular material from inside of the eye. The ocular material withdrawn from the eye is equally replaced with irrigation fluid provided through irrigation ports in an irrigation sleeve surrounding the aspiration needle. In the event the aspiration needle stops withdrawing ocular material, such as if it becomes occluded with a chunk of ocular material, irrigation fluid is directed to the outside of the eye via at least one irrigation aperture to keep the eye cool where the needle is ultrasonically vibrating.

11 Claims, 8 Drawing Sheets

(56) References Cited

U.S. PATENT DOCUMENTS

| | | | |
|---|---|---|---|
| 5,616,139 A * | 4/1997 | Okamoto | A61F 9/008 606/4 |
| 6,267,752 B1 * | 7/2001 | Svetliza | A61B 3/0008 600/205 |
| 7,762,978 B2 | 7/2010 | Mackool | |
| 8,475,480 B2 | 7/2013 | Mackool | |
| 9,211,137 B2 * | 12/2015 | Voic | A61B 17/142 |
| 2003/0053219 A1 | 3/2003 | Manzi | |
| 2008/0188792 A1 * | 8/2008 | Barrett | A61F 9/00745 604/22 |
| 2008/0281277 A1 * | 11/2008 | Thyzel | A61F 9/007 604/256 |
| 2012/0172786 A1 * | 7/2012 | Mackool | A61M 1/0084 604/22 |
| 2013/0331872 A1 | 12/2013 | Parham et al. | |
| 2016/0106580 A1 * | 4/2016 | Banko | A61F 9/008 604/22 |

\* cited by examiner

OCCLUSION-ACTIVATED HEAT SUPPRESSION INFUSION SLEEVE

CROSS-REFERENCE TO RELATED APPLICATIONS

This Divisional Patent Application claims priority to and the benefit of U.S. patent application Ser. No. 14/450,107, entitled: Occlusion-Activated heat Suppression Infusion Sleeve, filed on Aug. 1, 2014, which claims priority to and the benefit of U.S. provisional Patent Application No. 61/861,879, entitled: Occlusion-Activated heat Suppression Infusion Sleeve, filed on Aug. 2, 2013 the entire disclosure of which is hereby incorporated by reference.

FIELD OF THE INVENTION

The present invention is directed to a phacoemulsification device with cooling aperture ports that is useful in providing cooling to an eye during cataract surgery.

BACKGROUND OF THE INVENTION

A cataract is the clouding of the eye's natural lens. The lens is mostly made up of water and protein. As we age, these proteins change and clump together obscuring the lens. Correcting this change is generally done by removing the cataract lens and replacing it with a clear lens implant. One way of correcting the effects of cataracts is through Phacoemulsification eye surgery.

Phacoemulsification is a surgery technique on an eye wherein the internal lens is emulsified with a phacoemulsification, or phaco for short, needle tip driven to vibrate ultrasonically by an ultrasonic producing mechanism in the phaco handpiece. The ultrasonic vibration of the phaco needle creates a significant temperature rise of the needle. The temperature rise occurs essentially instantaneously. The emulsified lens material (mostly fluid) is aspirated from the eye through the phaco needle and replaced with an irrigation fluid made up of a balanced salt solution. Intraocular pressure (TOP) is maintained in the eye while the phaco needle is aspirating ocular material from the eye by constantly infusing saline solution into the eye. This constant replenishment of fluids in the eye is critical to avoid collapse of the anterior chamber of the eye. The irrigation fluid is also the only fluid that cools the heating effects of the vibrating phaco needle, thus preventing burning of eye tissue at the incision site. On occasion, large chunks of ocular material clog the phaco needle, which interrupts the aspiration flow, which in turn causes interruption in the irrigation flow. Though the irrigation flow is interrupted, the phaco needle may still be vibrating causing localized heating and potential localized burning of the eye.

It is to improvements in dealing with localized heating of the eye when aspiration flow is interrupted that embodiments of the present invention are directed.

SUMMARY OF THE INVENTION

The present invention is directed to a phacoemulsification device with cooling aperture ports that is useful in providing cooling to the incision site of an eye during cataract surgery.

Certain embodiments of the present invention can therefore comprise a phacoemulsification device comprising: a handpiece; an aspiration needle extending from the handpiece, the aspiration needle adapted to pull a volume of lens material at a particular rate from an eye via an aspiration port located at the distal end of the aspiration needle; an irrigation sleeve that surrounds a portion of the aspiration needle, the irrigation sleeve is spaced apart from the aspiration needle to provide an irrigation pathway where through liquid is adapted to flow; at least one irrigation port extending through the irrigation sleeve and providing an exit for the liquid to pass from the irrigation pathway outside of the phacoemulsification device, the irrigation port adapted to replace the volume of lens material with the liquid at the particular rate into the eye to maintain a balanced intraocular pressure in the eye, a portion of the aspiration needle, a portion of the irrigation sleeve, and the at least one irrigation port are adapted to be inserted inside of the eye; at least one aperture forming an outlet from the irrigation pathway and the phacoemulsification device through which a portion of the liquid can flow, the at least one aperture when in use is not adapted to be inserted inside of the eye, the aperture adapted to direct fluid towards the eye at an accelerated rate if the aspiration needle pulls less than the volume of lens material at the particular rate. In these embodiments, the aperture is adapted to direct the fluid towards the eye at a decelerated rate while the aspiration needle pulls the volume of lens material at the particular rate. In these embodiments, there can further be an irrigation sleeve hub disposed between the aspiration port and the handpiece wherein the irrigation sleeve hub possesses a hub diameter that is greater than a sleeve diameter of the irrigation sleeve, the at least one irrigation port located at the irrigation sleeve hub. Furthermore, the fluid that flows through the irrigation pathway is adapted to flow essentially at a continuous rate prior to reaching the aperture and the irrigation port whereby if the particular rate of the volume of the liquid slows through the irrigation port more of the liquid is adapted to flow through the aperture in order to maintain the continuous rate.

Other embodiments of the present invention can therefore comprise a method for using a phacoemulsification device for eye surgery comprising the steps of: providing the phacoemulsification device comprising a handpiece through which extends an irrigation sleeve and an aspiration needle, the aspiration needle extending distally from the irrigation sleeve surrounding a portion of the aspiration needle, the irrigation sleeve extending from the handpiece towards but not including the distal end of the aspiration needle wherein an inner surface of the irrigation sleeve and an outer surface of the aspiration needle are spaced apart through which irrigation fluid can flow, an irrigation port extending through the phacoemulsification device into the infusion sleeve, at least one aperture extending into the infusion sleeve, and a fluid source that provides the irrigation fluid to flow there from at essentially a constant supply pressure though the infusion sleeve; inserting the aspiration needle to at least include the irrigation port into an eye; after the inserting step, aspirating lens material from the eye through the aspiration needle at an aspiration flow rate; replacing the lens material with a sufficient amount of the irrigation fluid to maintain essentially constant intraocular pressure in the eye, the sufficient amount of the irrigation fluid flows through the infusion sleeve and through the irrigation port at essentially the aspiration flow rate; directing the irrigation fluid through the at least one aperture towards the eye when the aspiration flow rate at least slows down, the at least one aperture is not inserted in the eye. In this embodiment, the directing step occurs when the aspiration flow rate stops. Optionally, the aspiration flow rate at least slows down due to an occlusion of the lens material in the aspiration needle. In another embodiment, a portion of the irrigation fluid is always diverted through the at least one aperture to the eye, but the irrigation fluid is accelerated toward the eye when the aspiration flow rate at least slows down. This embodiment further contemplates providing a hub interposed between the handpiece and the irrigation sleeve wherein the aperture extends there through. It is further contemplated that the constant supply pressure is essentially identical as the lens pressure. Another embodiment contemplates the aperture extends through the irrigation sleeve.

Yet, other embodiments of the present invention can therefore comprise a phacoemulsification device comprising: a handpiece; an aspiration needle extending from the handpiece, the aspiration needle is hollow and is adapted to remove lens material there through by way of a suction device; an irrigation sleeve surrounding a portion of the aspiration needle, a distal end of the aspiration needle is not surrounded by the irrigation sleeve; a conduit spaced between the irrigation sleeve and the aspiration needle wherein irrigation fluid is capable of flowing through the conduit; at least one irrigation port in the irrigation sleeve adapted to provide an outlet for the irrigation fluid from the conduit to outside of the phacoemulsification device, the aspiration needle adapted to be inserted into an eye up to at least past the irrigation port, wherein constant pressure can be maintained in the eye via volumetric replacement of the removed lens material by flowing the irrigation fluid through the irrigation port; at least one aperture located between the handpiece and the irrigation port, the at least one aperture providing a passage from the conduit to outside of the phacoemulsification device, the at least one aperture not adapted to be inside of the eye, the aperture adapted to direct the irrigation fluid to the eye at an accelerated rate when flow of the irrigation fluid via the irrigation port is reduced. This embodiment further contemplates that the at least one aperture is adapted to direct the irrigation fluid towards the eye at a decelerated rate when flow of the irrigation fluid via the irrigation port is not reduced during eye surgery. This embodiment further contemplates that the irrigation fluid is received from a fluid source at essentially a constant source pressure, wherein when the aspiration port becomes blocked, the irrigation port stops flowing the irrigation fluid into the eye and the at least one aperture increases the fluid flow at the constant source pressure. It is further contemplated that an irrigation sleeve hub is disposed between the aspiration port and the handpiece wherein the irrigation sleeve hub possesses a hub diameter that is greater than a sleeve diameter of the irrigation sleeve, the at least one irrigation port located at the irrigation sleeve hub. It is further contemplated that the at least one aperture is smaller than the irrigation port.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving eye surgery.

Figure 1A:
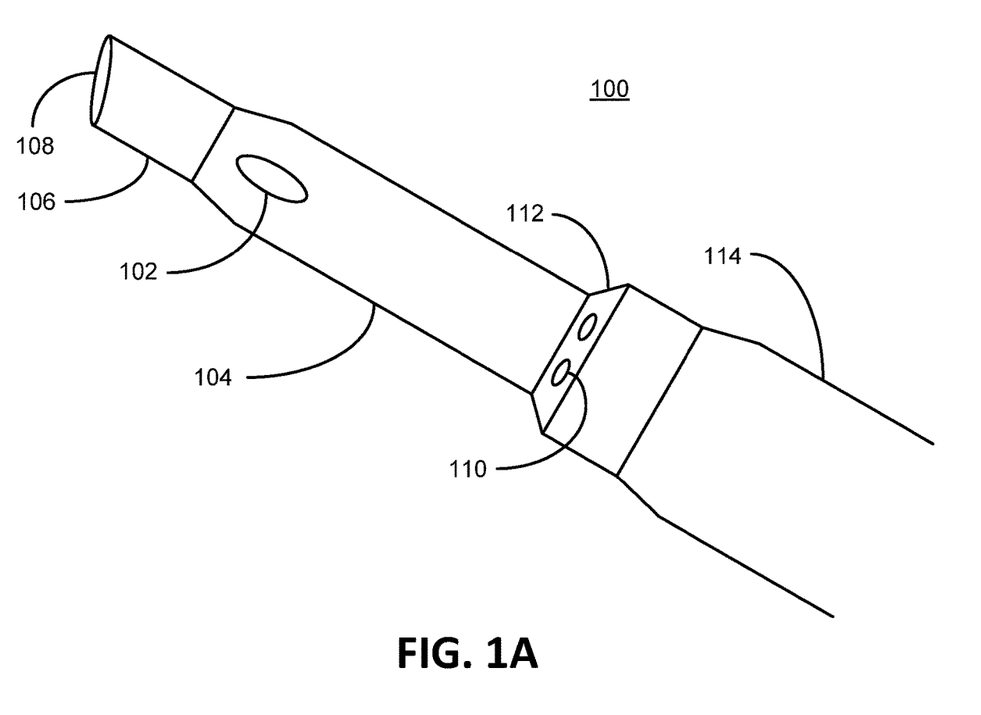
FIG. 1A illustratively depicts an embodiment of a phacoemulsification device consistent with embodiments of the present invention.
Figure 1B:
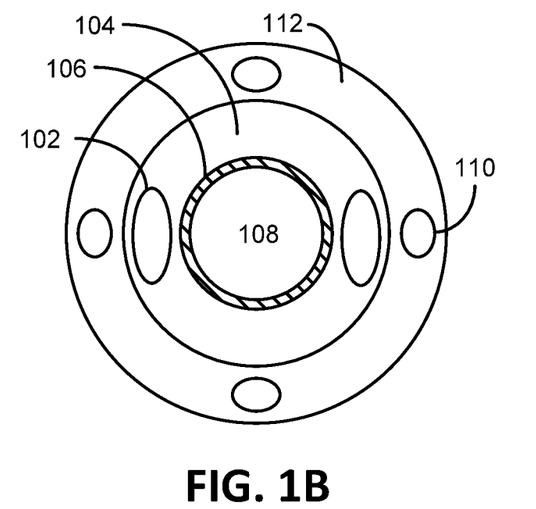
FIG. 1B illustratively depicts an embodiment of a front view of a phacoemulsification device consistent with embodiments of the present invention.

To illustrate an exemplary environment in which preferred embodiments of the present invention can be practiced, FIG. 1A depicts an embodiment of a phacoemulsification device 100 consistent with embodiments of the present invention. As shown the phacoemulsification device 100 generally comprises a handpiece 114, a hollow aspiration needle 106 extending from the handpiece 114, an irrigation sleeve 104 that surrounds a portion of the aspiration needle 106 (also known as a phacoemulsification needle), at least one irrigation port 102 extending through the irrigation sleeve 104, a hub 112, and at least one irrigation aperture 110 in the hub 112. FIG. 1B depicts a front view of FIG. 1A as viewed if one were looking down the hollow aspiration needle 106 through the aspiration port 108. As shown here, the irrigation sleeve 104 concentrically surrounds a portion of the aspiration needle 106 (the end of the aspiration needle 106 extends beyond the irrigation sleeve 104 depicted in FIG. 1A, for example). Also noted in the depiction of the present embodiment, which is non-limiting, the irrigation apertures 110 are equally dispersed around the hub 112. The hub 112, in this embodiment, concentrically surrounds a portion of the irrigation sleeve 104. A hub outer surface of the hub 112 is defined as the surface of the hub 112 that is interfacing or in contact with the outside environment and not covered or partially covered by any other component that makes up or is otherwise comprised by the phacoemulsification device 100, such as alternate sleeves or coverings. Covering the outside surface of the hub 112 by a person's hand does not change the definition of the hub outer surface. A sleeve outer surface of the irrigation sleeve 104 is defined as the surface of the irrigation sleeve 104 that is interfacing or in direct contact with the outside environment and not covered or partially covered by any other component that makes up or is otherwise comprised by the phacoemulsification device 100, such as alternate sleeves or coverings. As shown in FIG. 1A, the hub outer surface and the sleeve outer surface defines a contiguous outer surface in that the two surfaces are joined contiguously with a common boarder. More specifically, as shown the contiguous surface is one continuous surface in direct contact with the outside environment in that the outer surface is not obscured or even partially covered or shielded by other components, such as a cuff.

Figure 2:
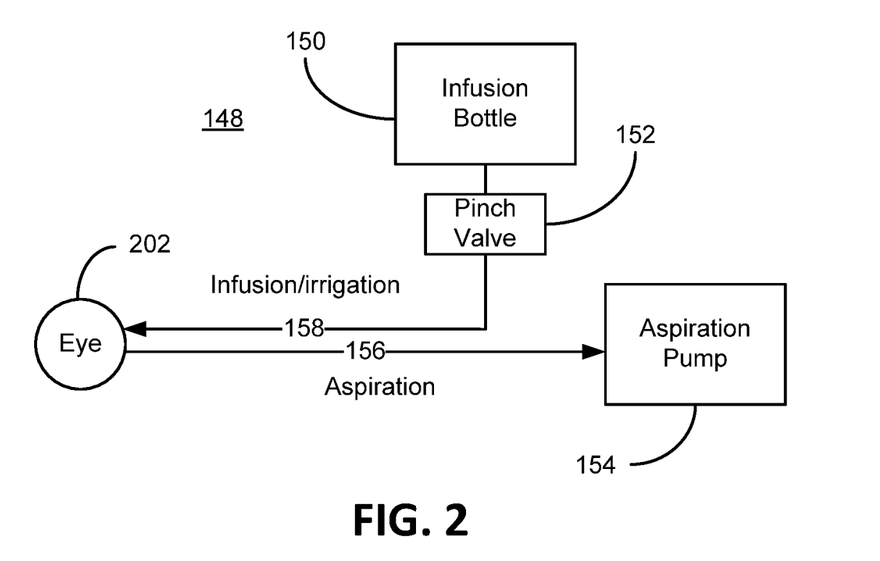
FIG. 2 depicts a system block diagram of a phacoemulsification system, consistent with embodiments of the present invention.

With reference to FIG. 2 in conjunction with FIG. 1, shown therein is a block diagram of a phacoemulsification system embodiment 148. As shown, the phacoemulsification system 148 includes an infusion bottle 150 of balanced salt solution generally positioned between 100 cm to 130 cm above the eye 202 (or to a level that gravitationally provides balanced intraocular pressure (TOP) in the eye 202 which is generally between 10 mm Hg and 20 mm Hg and averages to 15.5 mm Hg in a human eye. During a cataract surgery, a surgeon tries to keep the TOP above 20 mm Hg, especially after a vacuum surge). Osmotically balanced salt solution is compatible with the ocular fluid in the eye 202. The system 148 further provides a pinch valve 152 that opens and closes an infusion/irrigation pathway 158 to the eye 202. An aspiration pump 154 is adapted to suck emulsified lens material (ocular material) from the eye 202 through the aspiration port 108 at the distal end (tip) of the hollow aspiration needle 106. During a phacoemulsification procedure, the aspiration needle 106 is inserted through an incision in the anterior chamber of the eye 202 up to and including the irrigation port 102. The aspiration needle 106 is vibrated ultrasonically to break up (emulsify) lens material in the eye 202. The small pieces of the emulsified lens material are sucked through the hollow aspiration needle 106 away from the eye 202 along the aspiration pathway 156 by way of the aspiration pump 154. The aspiration pump 154 is adapted to pull (vacuum) a volume of emulsified lens material at a particular rate from the eye 202 by way of the aspiration port 108. Generally, the aspiration rate is approximately 5 cc of fluid/minute. Irrigation fluid replaces the removed lens material (at the same particular rate of aspirated lens material) by way of gravity from the infusion bottle 150 that is raised at an appropriate distance above the eye 202 to maintain TOP. The irrigation fluid flows (is discharged) into the inside of the eye 202 through the irrigation port 102 that is inside of the eye 202. In other words, the irrigation fluid replaces the lens material at the rate at which the lens material is removed from the eye 202 to maintain appropriate TOP, thus avoiding collapse of the anterior chamber of the eye 202. Hence, the irrigation flow rate into the eye essentially equals the aspiration flow rate from the eye. The word essentially is used here to indicate that at some level there flow rate is not exactly equal, but for all intents and purposes is more or less equal. The irrigation port 102 is a pathway into the irrigation sleeve 104, whereby irrigation fluid passes from the irrigation sleeve 104 out the irrigation port 102 into the eye 202. The irrigation sleeve is spaced apart from the aspiration needle 106 to form an irrigation pathway 158. The irrigation pathway 158 extends from the irrigation port 102, through the handpiece 114 to the infusion bottle 150.

Figure 3:
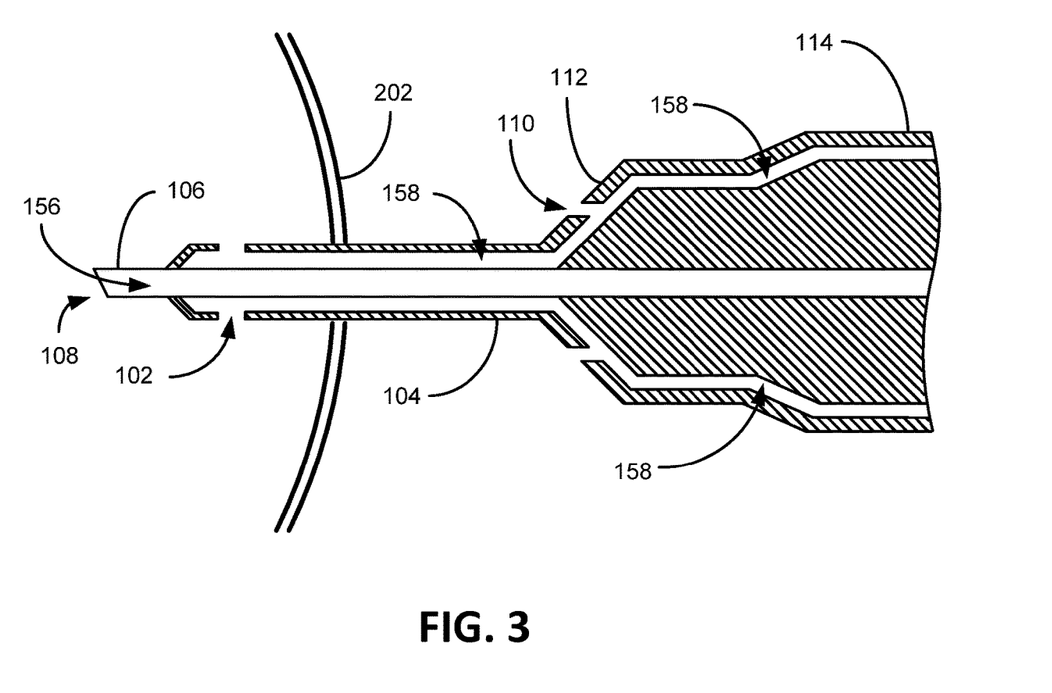
FIG. 3 illustratively depicts a cross section of a phacoemulsification device consistent with embodiments of the present invention.

FIG. 3 shows a cross section of the phacoemulsification device 100 of FIG. 1. The phacoemulsification needle 106 and irrigation ports 102 are located completely inside the eye 202. The aspiration pathway 156 extends from the aspiration port 108 through the hollow phacoemulsification needle 106 and handpiece 102. In the depicted embodiment, the irrigation sleeve 104 is spaced apart from the aspiration needle 106 to provide the irrigation pathway 158 where through irrigation fluid is adapted to flow. In this embodiment, the irrigation sleeve 104 is hollow. The irrigation pathway 158 extends through the handpiece 114 and to the infusion bottle 150. The irrigation port 102 is an opening into the irrigation sleeve 104, which provides an exit for the irrigation fluid to pass from the irrigation pathway 158 outside of the phacoemulsification device 100 and into the eye 202. As previously discussed, the irrigation fluid is adapted to flow through the irrigation port 102 to replace the volume of lens material/fluid aspirated from the eye 202 to maintain IOP. The irrigation flow rate into the eye 202 is essentially the same as the aspiration flow rate from the eye 202 (to balance the volume of fluid in the eye 202). As is also depicted, the irrigation sleeve hub 112 possesses at least one irrigation aperture 110 forming an outlet from the irrigation pathway 158 through which a portion of the irrigation fluid can flow. Certain embodiments contemplate the irrigation aperture 110 simply extending through the irrigation sleeve 104. The irrigation aperture 110 when in use is not intended to be inserted inside of the eye 202. Certain embodiments herein contemplate that no part of the irrigation aperture 110 comes into contact with the surface of the eye 202 (in contact with the eye 202 is intended to include touching, overlapping, near contact, or simply being at the eye surface. The intention in this embodiment is that the irrigation aperture 110 is spaced at least slightly away from the surface of the eye 202). For example, no part of the irrigation aperture 110 overlaps the eye 202 or touches the eye 202 in anyway. The irrigation aperture 110 stays away from the surface of the eye to direct irrigation fluid to the eye 202 when needed. Preferably, the irrigation aperture 110 is at least one-eighth (⅛) of an inch from the surface of the eye 202. One embodiment contemplates a phacoemulsification needle having dimensions wherein the irrigation port 102 is less than one-half of an inch from the aspiration port 108 (so that the irrigation port 102 remains within the eye 202) and the irrigation aperture 110 is at least three-quarters of an inch from the aspiration port 108. Other embodiments contemplate the irrigation port 102 less than the diameter of a dilated pupil (so the irrigation port 102 is always in the eye during the phacoemulsification procedure) and the irrigation aperture 110 is greater than the diameter of the dilated pupil (so the irrigation aperture 110 always remains outside of and not in contact with the eye 202). The irrigation aperture 110 is arranged to direct aspiration fluid towards the eye 202 at an accelerated rate if the aspiration needle 106 fails to pull lens material at the normal aspiration rate, which can occur when the aspiration needle 106 becomes occluded, or partially occluded, with a large, obstructing, piece of lens material 350. Normal aspiration rate (normal flow rate, or the rate at which ocular material is withdrawn from inside of an eye freely) is considered the aspiration rate of lens material at an unobstructed flow rate determined by the suction rate from the aspiration pump 154, which can be at a rate of 5 cc/minute in some eye surgery procedures. As should be appreciated, if there is a vacuum surge during aspiration, there will be essentially an equal influx of irrigation fluid into the eye 202 via the irrigation port/s 102.

Figure 4A:
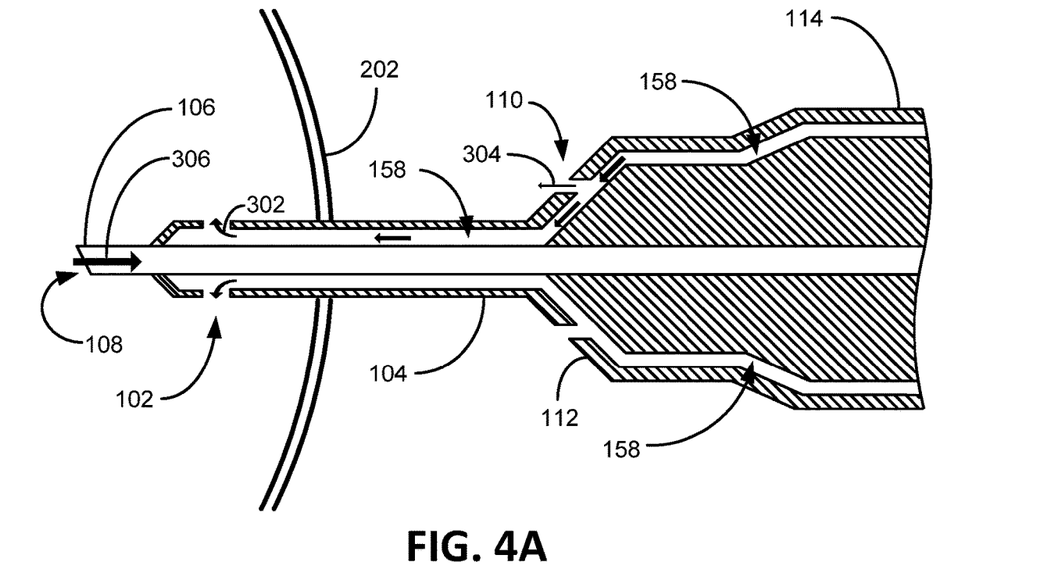
FIGS. 4A and 4B illustratively depict a cross section of a phacoemulsification device in operation consistent with embodiments of the present invention.
Figure 4B:
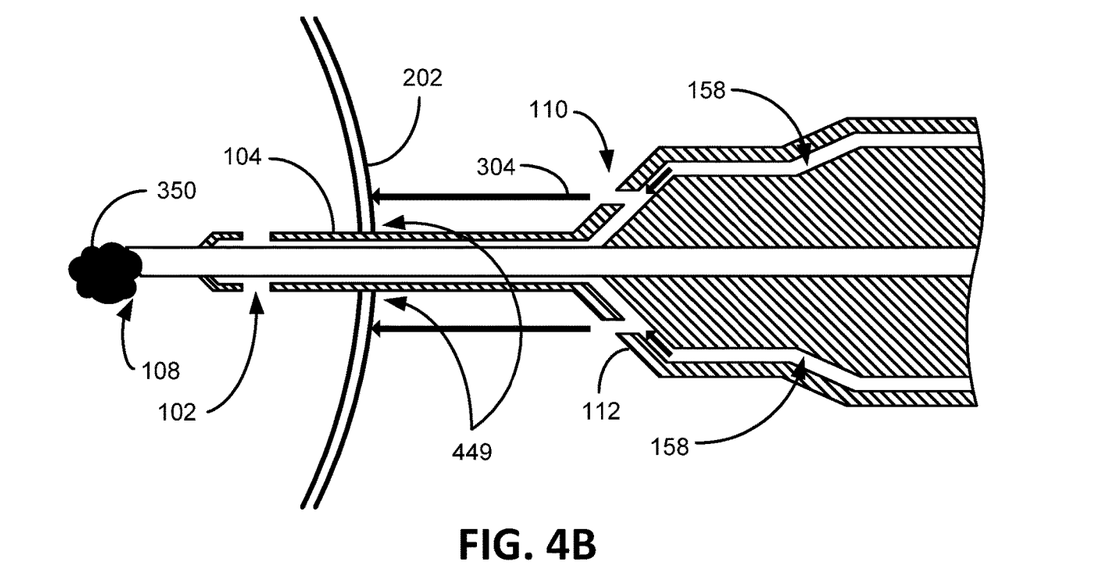

FIGS. 4A and 4B illustratively show the cross sections of the phacoemulsification device 100 in operation. As depicted in FIG. 4A, under normal operation, emulsified lens material is aspirated through the hollow phacoemulsification needle 106 as indicated by arrow 306. As also previously mentioned, in order to maintain TOP equilibrium, irrigation fluid replaces the aspirated lens material at the same rate the lens material is remove from the eye 202 by flowing through the irrigation port/s 102 as shown by the arrow 302. This can be accomplished by positioning the irrigation bottle 150 at a level above the eye 202 that can essentially maintain a TOP ("essentially maintained" because as the level of the irrigation fluid in the irrigation bottle 150 drops and pressure may change up and down a little between effects of aspiration and irrigation). In the present embodiment as illustratively depicted, while irrigation fluid flows 302 freely ("freely" is intended herein to mean without any flow reduction due to an occlusion or other flow interruption in the phacoemulsification needle 106) through the irrigation ports 102, the aperture 110 leaks irrigation fluid towards the eye 202 as indicated by the arrow 304. Certain embodiments contemplate the aperture 110 possessing a smaller opening than the irrigation port 102 to insure sufficient irrigation fluid to flow into the eye 202 via the irrigation port 102 based on irrigation port 102 being the path of least resistance for the irrigation fluid to exit the phacoemulsification device 100. Some benefits of the irrigation fluid directed towards the eye 202 via the aperture 110 during normal operation is to keep the outer portion of the eye 202 moist, which otherwise is typically done manually with eye droppers.

As illustratively shown in FIG. 4B, when a piece of lens material 350 occludes aspiration flow, shown here as lens material 350 lodged outside of the phacoemulsification needle 106 blocking the aspiration port 108 (but may be elsewhere along the aspiration pathway 156, such as in the aspiration needle 106), flow through the irrigation port/s 102 is halted due to the balanced hydrostatic pressure between the irrigation fluid pressurized at the infusion bottle level and the TOP in the eye 202. As the flow through the irrigation port/s 102 is halted, flow through the aperture 110 is accelerated towards the eye 202. This acceleration of irrigation fluid towards the eye 202 helps transfer heat created by the ultrasonically vibrating aspiration needle 106. Likely, the lens material 350 will break apart via the continued ultrasonic vibrations in the aspiration needle 106 and be aspirated away, thus resuming the normal flow of FIG. 4A. Because of the constant pressure created by the raised infusion bottle 150 (due to gravitational forces on the liquid in the infusion bottle 150 because it is raised above the eye 202), if there is a decrease in aspiration flow 306, there will be a decrease in the irrigation flow 302 through the irrigation port 102 and an increase in aperture flow 304 through the aperture 110.

Embodiments further contemplate that when the aspiration flow rate from the eye 202 decreases, the irrigation flow rate onto the eye 202 from the irrigation apertures 110 increases proportionally. Hence, for example, if there is an irrigation aperture flow rate of 0.2 cc/minute when ocular material is being aspirated freely at 5 cc/minute, if the aspiration flow rate slows to 2 cc/minute then the irrigation aperture flow rate will direct irrigation fluid to the outside of the eye 202 at 3.2 cc/minute. Or if the aspiration flow rate comes to a stop, the irrigation aperture flow rate will direct irrigation fluid to the outside of the eye 202 at 5.2 cc/minute. Other embodiments contemplate that when the aspiration flow rate is flowing freely (say at 5 cc/minute), there is no flow onto the outside of the eye 202 from the irrigation apertures 110, but if the aspiration flow rate slows to zero, the irrigation aperture flow rate increases proportionally (to say 5 cc/minute).

Other embodiments contemplate that the irrigation flow rate from the irrigation apertures 110 is zero until the aspiration needle 106 becomes occluded and the aspiration flow stops. Some embodiments contemplate that the irrigation flow rate from the irrigation apertures 110 flows at a rate of 1 cc/minute when spraying irrigation fluid onto the outside of the eye 202 assuming the aspiration flow rate is 5 cc/minute. As will be appreciated, the different flow rates described herein are by way of example and are merely embodiments of other flow rate ranges that can be reasonably used to withdraw ocular material from an eye 202 and replenish irrigation fluid into the eye 202, and if there is an occlusion causing rapid localized heating of the eye 202 where the aspiration needle 106 is ultrasonically vibrating without irrigation fluid flowing through the irrigation port/s 102 to cool the aspiration needle 106, irrigation fluid from the irrigation aperture/s 110 spray on the eye 202 to cool the incision site 449 of the eye 202 to help prevent burning of the ultrasonically vibrating aspiration needle 106.

Figure 5:
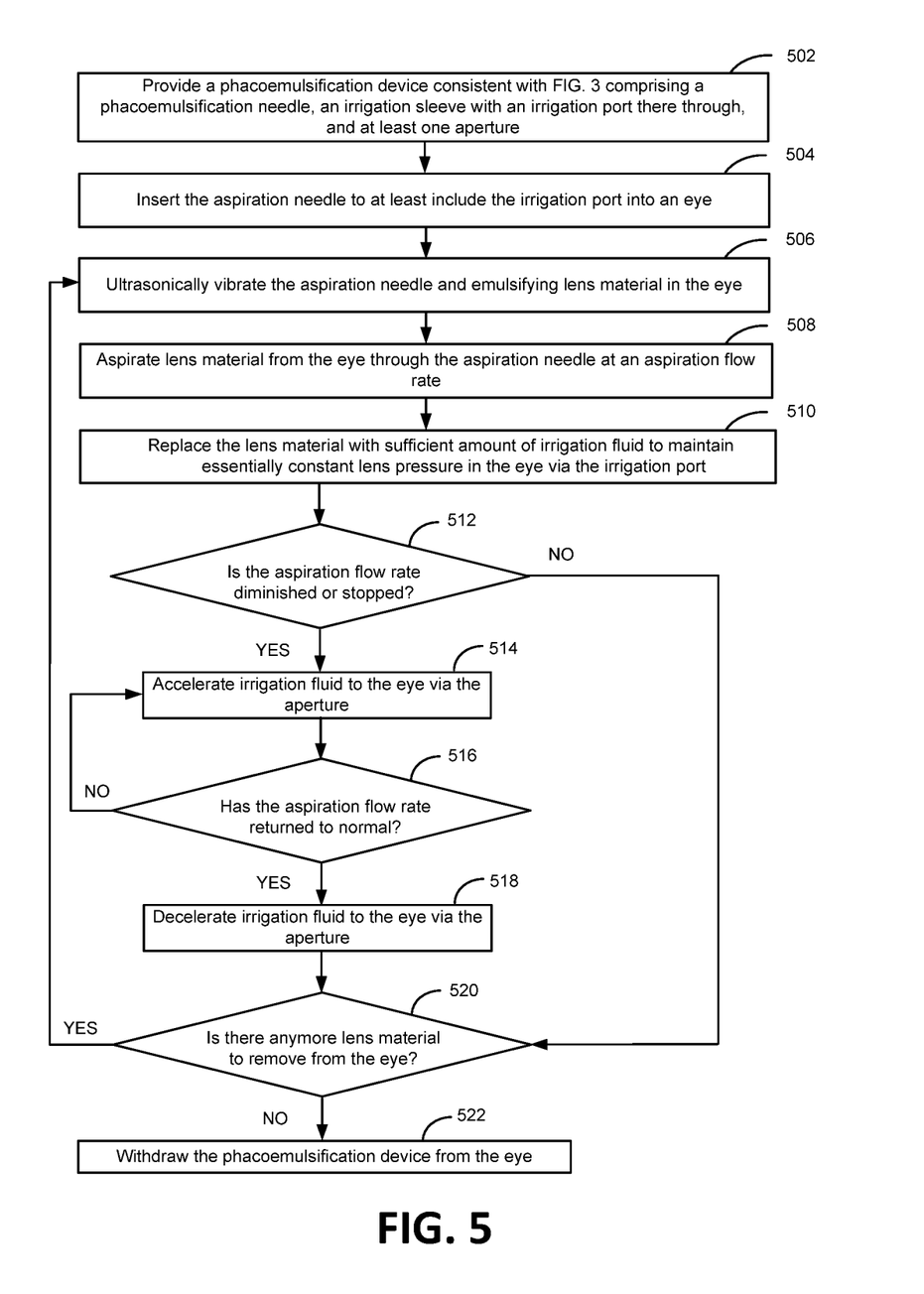
FIG. 5 depicts a block diagram of a method of use of an embodiment of the phacoemulsification device consistent with embodiments of the present invention.

FIG. 5 shows steps of a method embodiment for using the phacoemulsification device 100 for eye surgery consistent with embodiments of the present invention. Step 502 provides a phacoemulsification device 100 consistent with FIGS. 1A-4B, which generally comprises a handpiece 114 through which extends an irrigation sleeve 104 and an aspiration needle 106. The aspiration needle 106 extends distally from the irrigation sleeve 104 which surrounds a portion of the aspiration needle 106, whereby the distal end of the aspiration needle 106 is not covered by the irrigation sleeve 104 as depicted in FIG. 1. The irrigation sleeve 104 extends from the handpiece 114 towards the distal end of the aspiration needle 106 wherein an inner surface of the irrigation sleeve 104 and an outer surface of the aspiration needle 106 are spaced apart to create an irrigation flow channel/pathway 158 adapted to accommodate irrigation fluid. The irrigation sleeve 104 provides an irrigation port 102 which extends through the irrigation sleeve 104 into the irrigation flow space 158, at least one aperture 110 that extends into the irrigation flow space 158 (the aperture 110 is intended to remain outside of the eye 202), and a liquid source, such as the infusion bottle 150, that transfers irrigation liquid at essentially a constant supply pressure though the irrigation sleeve 104 and out through the irrigation port 102. Step 504 is a step for inserting the aspiration needle 106 to at least include the irrigation port 102 into an eye 202. Step 506 is a step for ultrasonically vibrating the aspiration needle 106 to emulsify lens material in the eye 202, such as to break up a cataract lens. Step 508 is a step for aspirating lens material from the eye 202 through the aspiration needle 106 at an aspiration flow rate after the inserting step 504 and while the aspiration needle 106 is ultrasonically vibrating. Step 510 is a step for replacing the lens material with a sufficient amount of the irrigation liquid to maintain essentially constant lens pressure in the eye 202. The sufficient amount of the irrigation liquid flows through the irrigation flow space and through the irrigation port 102 at the same rate as the aspiration flow rate (wherein the lens material is being aspirated). Step 512 is a decision step questioning if the aspiration flow rate has diminished or stopped. If the aspiration flow rate has not diminished or stopped then the process will continue smoothly to decision step 520. However, if the aspiration flow rate has diminished or stopped, such as due to an occlusion of lens material 350, then step 514 shows the response is to immediately accelerate irrigation fluid to the eye 202 by way of the aperture 102. As shown in step 516, if the aspiration flow rate has returned to normal, such as if the lens material 350 is no longer blocking the aspiration pathway 156 (the continued ultrasonic vibrations are likely to break up the lens material 350) then the irrigation fluid directed to the outer eye 202 through the aperture 102 is decelerated back to before the occlusion occurred, step 518, and the phacoemulsification procedure returns to normal, step 520. If the aspiration flow rate has not returned to normal (i.e., the lens material 350 is still blocking the aspiration pathway 156) then the high rate of irrigation fluid directed to the eye 202 through the aperture 110 of step 514 is continued). As shown in step 520, if all the lens material intended to be removed from the eye 202 is indeed removed, then withdraw the phacoemulsification device 100 from the eye 202, step 522. If there is still lens material to remove, proceed to step 506 and continue through the flow diagram.

Some embodiments contemplate the irrigation fluid to be continuously flowing at a low rate towards the eye 202 through the aperture 110, where in step 514 the low flow rate is increased to a high flow rate. Likewise, if in step 516 the aspiration flow has returned to normal, the flow rate of irrigation fluid towards the eye 202 is decelerated back to the low flow rate through the aperture 110. Other embodiments contemplate that the irrigation fluid is essentially not flowing through the aperture 110 if the aspiration flow rate is normal.

Some embodiments contemplate the aperture 110 in a location other than the sleeve hub 112, so long as the irrigation fluid can flow to the eye 202 as described.

Some embodiments contemplate the one or more apertures 110 smaller in diameter than the irrigation port 102. Because the irrigation fluid will flow through the point of least resistance, the irrigation port 102 being of larger diameter (or otherwise least resistance) will freely feed the eye 202 with irrigation fluid as needed. Certain embodiments contemplate aperture 110 diameter opening of between 0.002 inches to 0.02 inches.

Figure 6A:
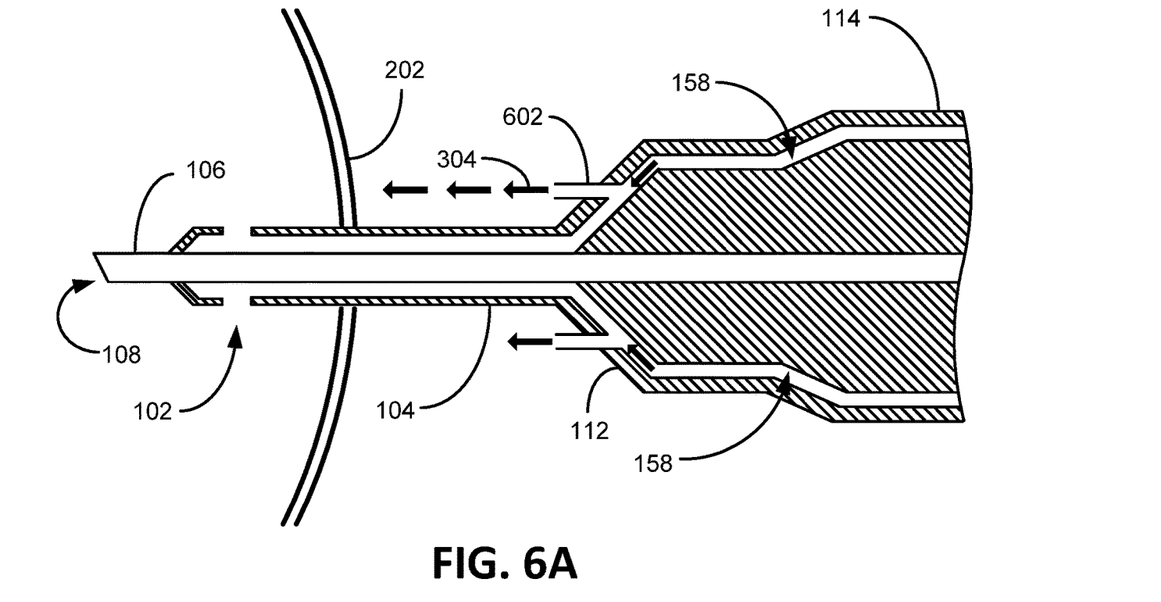
FIGS. 6A-6E depict alternative aperture embodiments consistent with embodiments of the present invention.
Figure 6B:
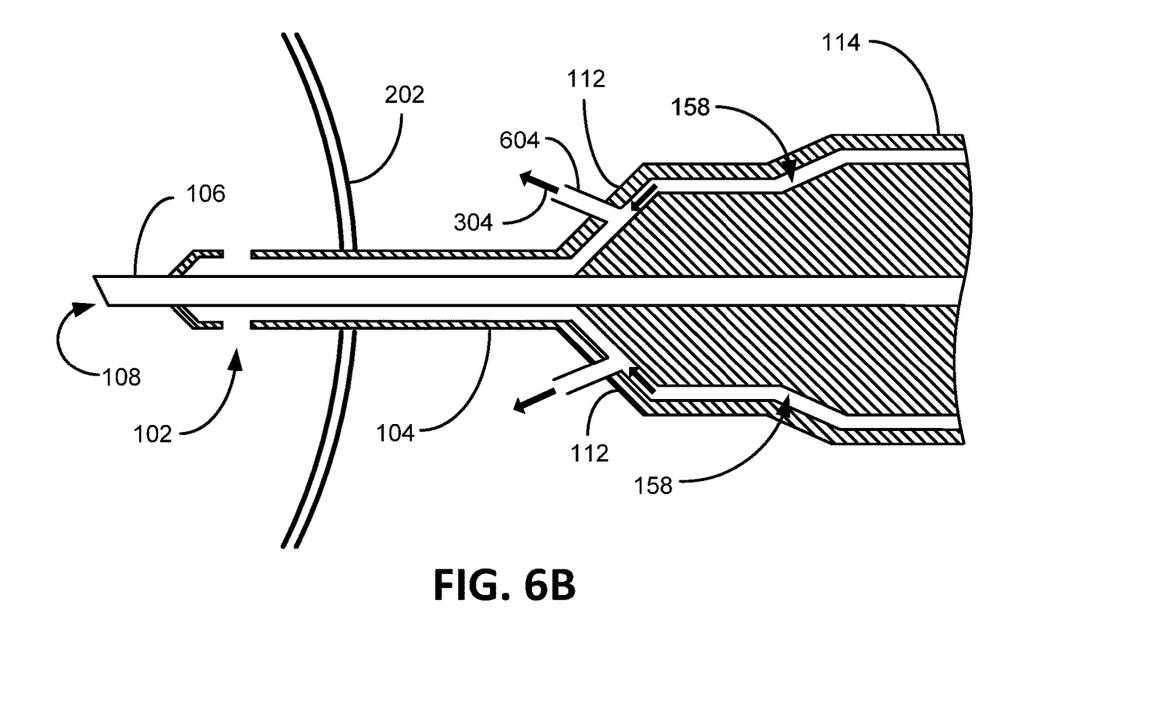
Figure 6C:
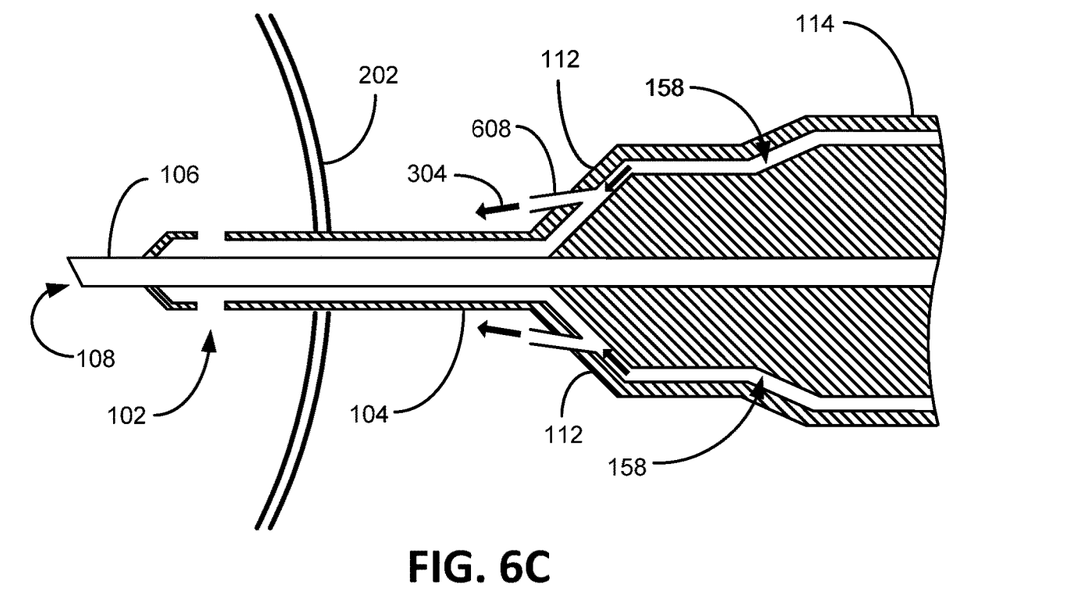
Figure 6D:
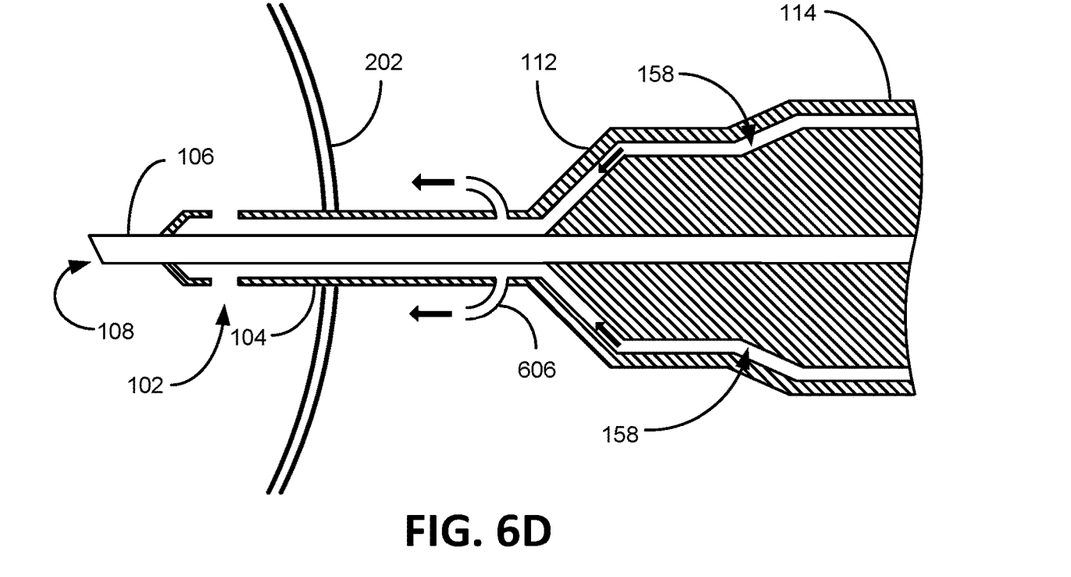
Figure 6E:
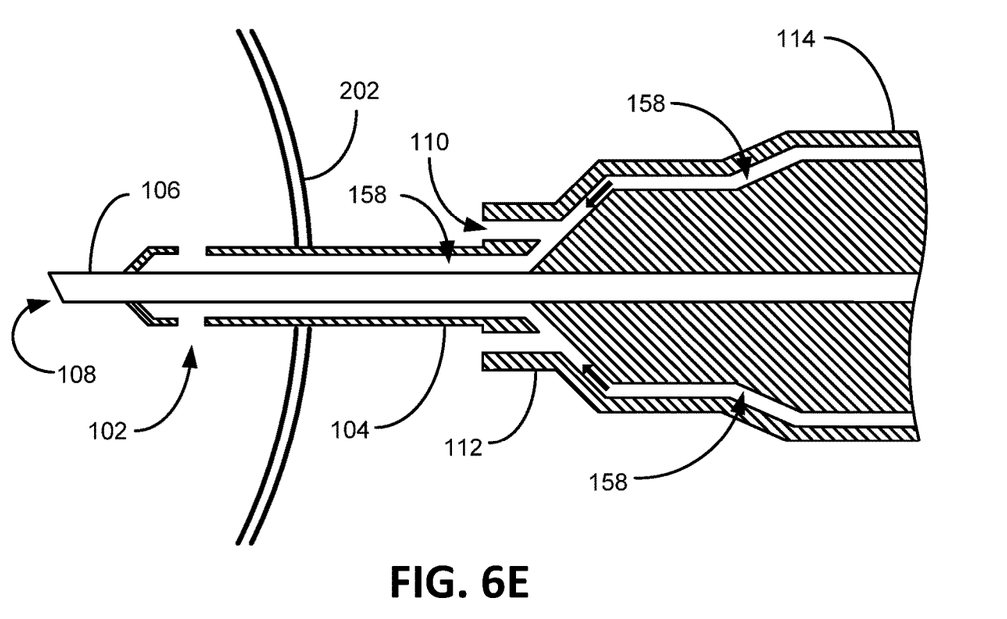

FIGS. 6A-6D illustratively depict alternative aperture embodiments consistent with embodiments of the present invention. FIG. 6A depicts an aperture insert tubing 602 extending from the irrigation hub 112 that directs irrigation flow 304 towards the eye 202 parallel to the aspiration needle 106. One embodiment of FIG. 6A contemplates the tubing 602 being a "stent" that creates a rigid opening to be maintained in a flexible irrigation sleeve 104, such as if the irrigation sleeve were latex or some other elastic material that would tend to close around a hole (an aspiration hole). FIG. 6B depicts an aperture insert tubing 604 extending from the irrigation hub 112 that directs irrigation flow 304 towards the eye 202 at an angle tilted away from the aspiration needle 106. FIG. 6C depicts an aperture insert tubing 606 extending from the irrigation hub 112 that directs irrigation flow 304 towards the eye 202 at an angle tilted towards from the aspiration needle 106. FIG. 6D depicts an aperture insert tubing 608 (an irrigation aperture embodiment) extending from the irrigation sleeve 104 that directs irrigation flow 304 towards the eye 202 at a bend so not to be obstructed by the aspiration needle 106. FIG. 6E depicts and embodiment of the irrigation hub 112 extending from the handle 114. In certain embodiments, the aperture insert tubing is conceived to be composed, made of, metal or plastic with aperture port diameter openings from between 0.002 inches to 0.02 inches with a length between 0.005 inches to 0.5 inches.

Some embodiments contemplate the irrigation sleeve 104 being comprised of a pliable material such as silicone, for example. Other embodiments contemplate the irrigation sleeve 104 being rigid with a pliable coating, such as silicone. Yet, other embodiments contemplate the irrigation sleeve 104 being rigid with no pliable coating whatsoever.

Some embodiments contemplate the aperture 110 possessing a valve system that essentially immediately responds by opening the aperture 110 to a reduction in irrigation fluid flow through the irrigation port 102. Such a valve is contemplated to be mechanical or electro-mechanical.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, the irrigation fluid comprised of a salt solution that is osmotically balance with the eye 202 is well known in the art and can be interchanged with other fluids with similar viscosity while still maintaining substantially the same functionality without departing from the scope and spirit of the present invention. In another example, the aperture 110 can be configured differently from one or more holes in the irrigation sleeve hub 112 without departing from the scope and spirit of the present invention, such as a tube configured differently than that shown for example, so long as aperture 110 directs irrigation fluid externally to the eye 202 at an accelerated rate when the aspiration pathway 156 becomes blocked or partially blocked. Though embodiments are described herein with an irrigation sleeve 104 concentrically surrounding the aspiration needle 106, other embodiments contemplate the irrigation sleeve 104 configured differently so long as irrigation fluid is delivered to an eye 202 within the scope and spirit of the present invention. The preferred embodiments described herein are directed to a phacoemulsification device 100, which accordingly is not intended for uses beyond the scope and spirit of eye surgery.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. An eye surgery method comprising:
providing a phacoemulsification device comprising a hollow aspiration needle possessing an aspiration port at a distal end of the aspiration needle;
a sleeve hub defining a hub outer surface;
an irrigation sleeve that surrounds the aspiration needle except for a tip region of the aspiration needle that includes the distal end, the tip region extends from the irrigation sleeve, the irrigation sleeve defining a sleeve outer surface and a sleeve inner surface;
an irrigation flow channel passing through the sleeve hub and between the aspiration needle and the sleeve inner surface;
a contiguous outer surface defined by the hub outer surface and the sleeve outer surface joined contiguously, the contiguous outer surface directly interfacing an outside environment;
an irrigation port extending from the sleeve inside surface through the sleeve outer surface;
an irrigation aperture extending from the irrigation flow channel to an outer surface location, that is proximal to the irrigation port, on the collective outer surface;
inserting the tip region and a portion of the irrigation sleeve including the irrigation port into an eye; ultrasonically vibrating the aspiration needle;
aspirating ocular material from inside of the eye through the aspiration port at an aspiration flow rate;
discharging the irrigation fluid through the irrigation port into the eye at an irrigation port flow rate, the irrigation port flow rate essentially equals the aspiration flow rate;
directing the irrigation fluid through the irrigation aperture towards the outside of the eye at an aperture irrigation flow rate, the irrigation aperture does not come into contact with the eye.

2. The eye surgery method of claim 1 wherein the aperture irrigation flow rate is zero when the ocular material flows freely through the aspiration port during the aspirating step, but the aperture irrigation flow rate increases when the aspirating flow rate decreases.

3. The eye surgery method of claim 2 wherein the aperture irrigation flow rate is inversely proportional to the aspiration flow rate.

4. The eye surgery method of claim 1 wherein the aperture irrigation flow rate is greater than zero when the ocular material flows freely through the aspiration port during the aspirating step, but the aperture irrigation flow rate increases when the aspirating flow rate decreases.

5. The eye surgery method of claim 4 wherein the aperture irrigation flow rate changes at a rate that is inversely proportional to the aspiration flow rate.

6. The eye surgery method of claim 1 further providing a handpiece from which the aspiration needle and the irrigation sleeve extend, the irrigation aperture is between the handpiece and the irrigation port.

7. The eye surgery method of claim 1 wherein the irrigation sleeve concentrically surrounds a portion of the aspiration needle.

8. The eye surgery method of claim 7 wherein said sleeve hub extends from a handpiece, the sleeve hub is closer to the aspiration port than the handpiece, the irrigation sleeve hub comprising a hub diameter defined by a location on the hub outer surface, the hub diameter is greater than a sleeve diameter defined by sleeve outer surface, the irrigation aperture located at the irrigation sleeve hub.

9. The eye surgery method of claim 1 wherein the irrigation aperture remains at least one-eighth of an inch from the eye during the aspirating step, the discharging step, and the directing step.

10. The eye surgery method of claim 1 wherein the directing step only occurs if the aspiration flow rate essentially goes to zero.

11. The method of claim 1 further controlling the irrigation fluid through the at least one irrigation aperture either manually or automatically.

\* \* \* \* \*